United States Patent [19]
Otten

[11] Patent Number: 5,255,691
[45] Date of Patent: Oct. 26, 1993

[54] PERCUTANEOUS EPIDURAL LEAD INTRODUCING SYSTEM AND METHOD

[75] Inventor: Lynn M. Otten, Blaine, Minn.

[73] Assignee: Medtronic, Inc., Minneapolis, Minn.

[21] Appl. No.: 790,928

[22] Filed: Nov. 13, 1991

[51] Int. Cl.⁵ .................................... A61N 1/05
[52] U.S. Cl. .................................... 607/117
[58] Field of Search ............... 128/784, 785, 786, 642

[56] References Cited

U.S. PATENT DOCUMENTS

| | | | |
|---|---|---|---|
| 4,512,351 | 4/1985 | Pohndorf | 128/786 |
| 4,549,556 | 10/1985 | Tarjan | 128/785 |
| 4,596,559 | 6/1986 | Fleischacker | 604/170 |
| 4,650,472 | 3/1987 | Bates | 604/158 |
| 4,744,371 | 5/1988 | Harris | 128/786 |
| 4,772,266 | 9/1988 | Groshong | 604/164 |
| 4,805,625 | 2/1989 | Wyler et al. | 128/642 |
| 4,919,653 | 4/1990 | Martinez et al. | 604/117 |
| 5,002,053 | 3/1991 | Garcia-Riu et al. | 128/421 |
| 5,031,618 | 7/1991 | Mullett | 128/421 |

OTHER PUBLICATIONS

B-D Products Catalog, by Becton-Dickinson, p. 58 *Tushy Epidural Anesthesia Needle-Sterile, Single-Use.*

*Primary Examiner*—William E. Kamm
*Assistant Examiner*—Scott M. Getzow
*Attorney, Agent, or Firm*—Harold R. Patton; Terry L. Wiles

[57] ABSTRACT

An improved method and apparatus for introducing a flexible member into the epidural space of the spinal column of a patient employing an introducer assembly for achieving access to the epidural space. The introducer assembly includes an epidural needle assembly, including an elongated needle having a side opening at its distal tip, a hub at its proximal tip and a lumen extending therebetween, and a stylet removable insertable within the lumen of said needle through said hub and having a beveled tip and a hub. The distal tip may be curved in the direction of the side opening when unrestrained by the stylet. The introducer assembly has a locking mechanism which preferably includes a lug extending from the side of the needle hub and an L-shaped cut-out in the side of the stylet hub for receiving the lug therein and allowing its rotation 90° to effect a bayonette-style locking of the two hubs.

22 Claims, 2 Drawing Sheets

PERCUTANEOUS EPIDURAL LEAD INTRODUCING SYSTEM AND METHOD

BACKGROUND OF THE INVENTION

1. Field of the Invention

The present invention relates to a method and apparatus for the introduction of a percutaneous flexible lead member and, particularly, to a method and apparatus for the introduction of a flexible neurostimulator lead into the epidural space of the spinal cord of a patient.

2. Description of the Prior Art

Chronically implantable stimulators for the brain and spinal cord have been in use for some time. Originally these were used to treat chronic intractable pain. Clinically favorable results were reported in a number of publications including "Long Term Follow Up of Dorsal Cord Stimulation for Chronic Pain Syndrome After Multiple Lumbar Operations", *Applied Neurophysiology*, Volume 45, pages 201-204, 1982 by J. Siegfried and Y. Lazorthes and "Spinal Epidural Neurostimulation for Treatment of Acute and Chronic Intractable Pain: Initial and Long Term Results", *Neurosurgery*, Volume 5, pages 344-348, 1979, by R. R. Richardson, et al.

Subsequently, additional medical applications were reported including treatment of peripheral vascular disease as seen in "Spinal Cord Stimulation in Peripheral Vascular Disease" *Proceedings on Functional Electrostimulation*, 1983, by E. H. Sedgwick, L. S. Illis, and R. C. Tallis. Research continues in the possible treatment of angina and other disorders by spinal cord stimulation. Spinal cord stimulation also has been used in treating multiple sclerosis, spinal cord injury, cerebral palsy, amyotrophic lateral sclerosis, dystonia, torticollis and other neurological disorders. The use of electrical stimulation of peripheral nerves and spinal cord to promote recovery from trauma and to accelerate nerve regeneration also has been proposed. In addition, spinal cord stimulation has been proposed to induce locomotion.

The earliest practical spinal cord stimulators were passive devices which picked up RF energy transmitted across the skin and applied it via electrodes implanted near the spinal cord. Many medical applications are yet best approached with such a device. The PISCESä family of spinal cord stimulation systems made available to the medical community by Medtronic, Inc. of Minneapolis, Minn., assignee of the present invention, are examples of passive spinal cord stimulation systems.

A later development in neurological stimulation is the chronically implantable active stimulation system. These consist of a battery operated pulse generator which is electrically coupled to the spinal cord by insulated leads coupled to electrodes normally implanted in the epidural space. The Itrel IIä implantable pulse generator manufactured by Medtronic, Inc., is an example of an active device that has advanced programmable features permitting mode changes by transcutaneous RF telemetry. These mode changes include modifying the stimulation intensity. A number of different lead designs have been employed for placement of one or more electrodes in the epidural space including the PISCES-SIGMAä GENERATION II or PISCESä GENERATION II epidural leads available from Medtronic, Inc.

These neural stimulation electrodes and leads implanted in the epidural space of the spinal cord of a patient for stimulating selected locations along the spinal cord, usually for the relief of pain. The leading distal end of the lead is axially moved along the epidural space in the spinal cord by passing the end through a Tuohy needle and pushing the end of the lead to the location on the dura where it is to stimulate the spinal cord. These leads have a special configuration at their distal ends and adjacent the stimulating electrodes which may be straightened during installation of the lead by a stylet which passes through the lead to ease its introduction. Once the lead has been positioned as desired, the lead stylet is removed to cause the distal end of the lead to resume its normal configuration to minimize subsequent axial or lateral movement of the lead once it has been placed. In these leads, the leading distal end of the lead is inaccessibly located in the epidural space at all times during introduction and fixation and, therefore, is capable of being manipulated, only from the other end thereof.

The aforementioned installation and fixation procedure is illustrated in FIGS. 1 and 2, which depict the operative procedure of introducing one of the aforementioned leads into the epidural space 10 adjacent the spinal cord 12. A Tuohy needle 14, which is usually between 14 and 18 gauge, and a stylet for stiffening the thin-walled needle are inserted into the interspinous ligament between adjacent vertebrae 20 and 22 until the tip of the needle is advanced through the ligamentum flavum and into the epidural space 10. The stylet is then withdrawn and a wire guide is inserted through the needle into the epidural space under fluoroscopic control to identify the pathway that the lead will take.

Penetration of the ligamentum flavum may be confirmed by withdrawing the stylet and filling the needle lumen with saline solution, which rapidly drains when penetration is achieved. The operative procedure is repeated until an appropriate pathway is identified.

Thereafter, the wire guide is removed and one of the aforementioned leads is inserted through the needle through the epidural space. Under fluoroscopic control, the lead is advanced to an appropriate spinal level under manipulation of the needle and lead itself. The lead depicted in FIG. 2 in the epidural space possesses a relaxed curved shape which is straightened during insertion by the lead stylet 22 shown extending from the straight-line connector 24 of the proximal end of the lead body. Once the lead has been positioned as desired, and electrical stimulation tests have been completed, the proximal end of the lead is coupled to the PISCESä spinal cord stimulation system RF receiver or the Itrel IIä implantable pulse generator.

The Tuohy needle and stylet conventionally used in such implants possesses a sharpened, curved Huber tip with a side opening to facilitate both the penetration of the subcutaneous fascia as well as the underlying interspinous ligament and ligamentum flavum and the direction of the wire guide and implantable lead at an angle to the axis of the introducer sheath as shown in FIGS. 1 and 2. The stylet is provided with a matching beveled end such that when it is fully inserted into the lumen of the introducer, the beveled surface may be lined up to the side opening to both stiffen the entire assembly and block the opening in the distal end of the needle, thereby easing its introduction. To avoid the inadvertent rotation of the stylet within the lumen of the needle during percutaneous advancement of the assembly, it has been conventional to provide a notch in the introducer hub which receives a complimentary lug on the stylet hub, as shown in FIGS. 2 and 3 of U.S. Pat. No. 4,512,351. During introduction, as shown for example in FIG. 7 of the '351 patent, manual force is applied to the two hubs to maintain the lug within the notch and prevent the inadvertent rotation or backing out of the stylet.

During such introduction, there is a tendency for the stylet to telescopically retract within the sheath when the medical attendant, nurse, doctor or the like is attempting to forcibly advance the tapered leading tip of the assembled introducer needle and stylet through the aforementioned tissue. This makes manipulation of the needle and stylet not only traumatic to the patient, but also awkward and imprecise for the medical attendant, who has to make certain that the stylet is not retracting or rotating in the process.

SUMMARY OF THE INVENTION

It is, accordingly, a primary object of the present invention to provide a novel needle/stylet assembly, and related methods.

It is a further dominant object of the present invention to provide a novel introducer needle/stylet assembly which insures a stable axial and rotational relationship between the superimposed needle and stylet during insertion.

In brief summary, the present invention comprises needle/stylet assemblies, and related methods, used in unstressed placement of catheters or leads into body cavities of medical patients, which invention overcomes or substantially alleviates the aforementioned problems of the prior art. The present invention insures a stable axial and rotational relationship between the assembled needle and stylet so that use is very facile for the medical attendant and insures a predetermined penetration of the puncture site to accommodate unstressed placement of a lead or catheter in the body cavity with minimal trauma to the patient.

These and other objects and advantages are realized in an apparatus and method of use thereof for introducing a flexible lead member into the epidural space in the spinal column of a patient through the use of an epidural needle assembly comprising an elongated introducer needle having a side opening at its distal tip and a lumen extending from the distal tip to a proximal hub attached to the needle at its proximal end and an elongated stylet having a hub at one end thereof and a pointed tip adapted to be positioned in the lumen of said needle to block the passage of fluids therethrough and to stiffen the needle, wherein the improvement comprises a locking mechanism comprising a first locking member on said hub of said needle and a second locking member on the hub of said stylet for locking the position of the stylet within said lumen of said needle and preventing relative axial or rotational motion therebetween, whereby said introducer needle and stylet assembly may be percutaneously inserted together between the vertebrae in the patient's spine so that the tip of the assembly is adjacent the epidural space of the patient when the assembly is so inserted.

This needle assembly is not limited to use with any specific lead or catheter, but can be used for any and all epidural, intrathecal, venous or arterial catheter introductions depending on the size of the cannula which is optional. For example, the needle assembly could be used in biopsy applications where precise and accurate placement is required. The needle assembly could also be used for cardiac lead introduction or drug delivery applications.

In preferred embodiments, the locking means further comprises a lug projecting from said hub of said stylet and an L-shaped cut-out in said hub of said needle, wherein said lug is adapted to be received in said L-shaped cut-out and said stylet is locked in place by relative rotation of said stylet hub with respect to said needle hub to advance and rotate said lug to a predetermined position in said L-shaped cut-out. Preferably said stylet and said needle have predetermined relative lengths such that said stylet, when in said locked position, completely fills the lumen of said needle and blocks said distal side opening thereof and said stylet has a beveled distal tip set at a predetermined angle to said lug whereby rotation of said lug to said predetermined position positions said beveled tip adjacent said side opening.

In a further preferred embodiment, the tip of the needle can itself be constructed of a shape retentive alloy (e.g., Elgiloy) with a 15° to 18° angle or bend pre-molded into the distal tip. When the stylet is inserted, the angled or bent distal tip becomes straight, allowing for ease of puncture. When the distal tip is in the epidural space, the stylet is removed and the curve or angle returns. This curve or angle enhances the stearability of the percutaneous lead or catheter introduced through the needle.

BRIEF DESCRIPTION OF THE DRAWINGS

These and other objects, advantages and features of the present invention will be apparent from the detailed description taken with reference to the accompanying drawings wherein like numerals are used to designate like parts throughout, and wherein.

DETAILED DESCRIPTION OF THE PREFERRED EMBODIMENTS OF THE INVENTION

Figure 1:
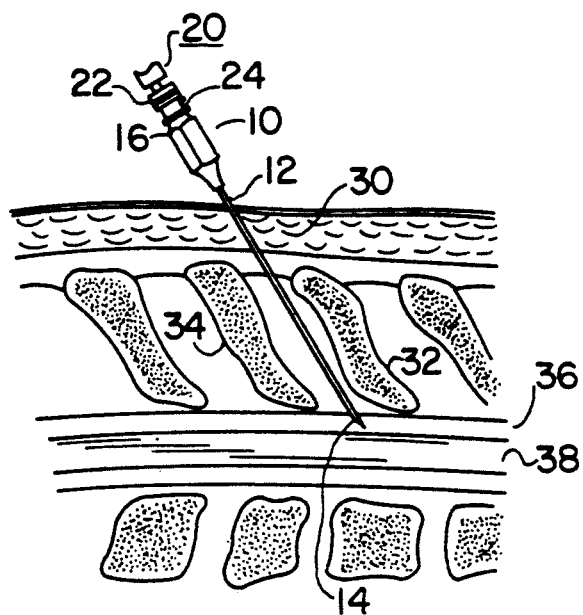
FIG. 1 is a perspective representation in partial cross-section of the percutaneous insertion of the assembled introducer needle and stylet.
Figure 2:
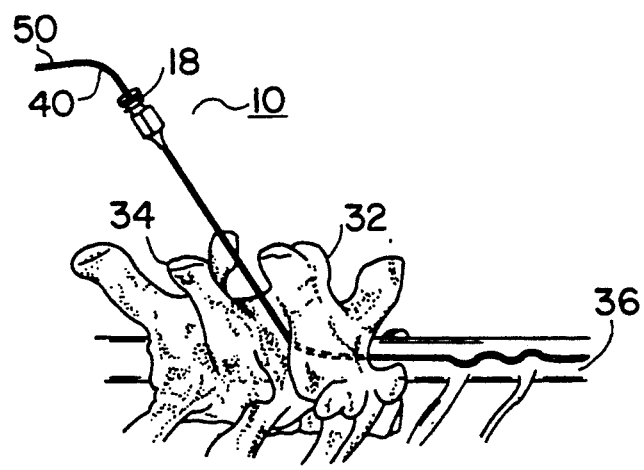
FIG. 2 is a perspective representation of the advancement of a lead and stylet into the epidural space.

In the drawings, FIGS. 3-6 illustrate a presently preferred introducer needle/stylet assembly for use in the procedure depicted in FIGS. 1 and 2 for introducing a lead into the epidural space for chronic stimulation of the spinal column in the manner described above. In FIG. 1, the assembled stylet 20 and introducer needle 10 are shown with the introducer needle 12 penetrating the subcutaneous fascia 30 and extending between adjacent vertebrae 32 and 34 until the distal tip 14 is positioned in the epidural space 36 and adjacent to the spinal cord 38 in the well known, above-described fashion.

In accordance with the improvement of the present invention, the hub 16 of the introducer 10 and the hub 22 of the stylet 20 are provided with a locking mechanism including the lug 24 which cooperates with an L-shaped cut-out in the hub 16 to line up the stylet tip 26 with the needle tip 14 and to hold that alignment during the advancement depicted in FIG. 1.

Turning now to FIG. 2, the needle 10 is depicted in a further view in relation to the vertebrae 32 and 34 and the epidural space 36 in order to show the introduction of the stimulation lead 40 and its lead stylet 50 after withdrawal of the stylet 20 in a fashion well known in the prior art. FIGS. 1 and 2 thus illustrate the operative steps of the procedure for attaining access to the epidural space 36 as well as the introduction of the epidural stimulating lead 40 and its associated electrodes and fixation mechanism therein. FIG. 1 in addition depicts in part the improved locking mechanism of the present invention.

Figure 3:
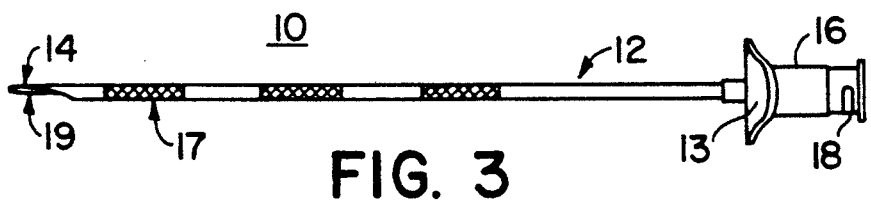
FIG. 3 is a side view of an epidural introducer Tuohy needle with a bayonette-style locking hub in accordance with the present invention.
Figure 4:
FIG. 4 is a side view of the improved locking stylet of the present invention.

Turning now to FIGS. 3 and 4, they depict the elements of the introducer 10 and the stylet 20 in greater detail. The introducer 10 includes the elongated needle 12 which typically has an outside diameter of between 14 and 18 gauge and an inside lumen diameter of 0.015 inches and is constructed of stainless steel. The needle 12 has a series of grit-blasted, 1 cm wide markings 16 along its length, each separated by 1 cm to provide the physician with an indication of the depth to which the needle/stylet assembly has been inserted in the implant procedure depicted in FIG. 1.

Finger engageable wings 13 coupled to introducer hub 16 allow the needle/stylet introducer assembly to be grasped with one hand leaving the other hand free to grip the needle shaft to carefully apply penetration force thereto. The distal tip 14 possesses an elongated Huber point opening 18 along one side thereof that is relatively flexible and easily bent in the epidural space after the stylet 20 is withdrawn to provide a curved guiding surface for the guide wire and lead introduced therethrough.

Referring now to FIG. 4, it illustrates a side view of the stylet 20 which may be constructed of a length of solid stainless steel 22 having a beveled sharpened tip 26 at its distal end for matching with the beveled opening Huber point 18 of the distal tip 14 of the needle 12. The hub contains the upstanding lug 24 which is about 0.6 inches long and 0.040 inches diameter.

Figure 5:
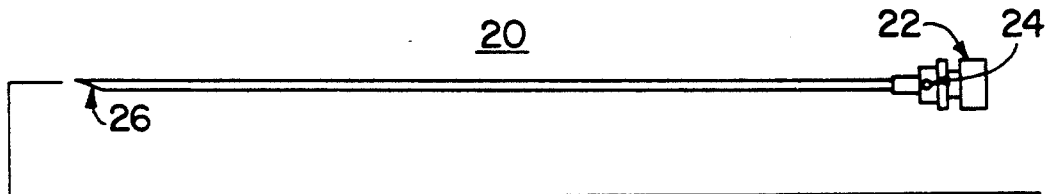
FIG. 5 is a side view depicting the manner in which the stylet of FIG. 4 is advanced into the needle of FIG. 3 such that the lug on the stylet hub fits within the notched opening of the bayonette connector on the hub of the introducer needle.
Figure 6:
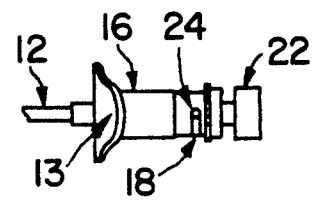
FIG. 6 is an enlarged detailed view of the assembly of the lug of the stylet hub into the hub of the needle.

The improved locking mechanism of the present invention is illustrated in FIG. 3 in conjunction with the hub 16 which possesses an L-shaped cut-out opening 18 which receives the lug 24 on the stylet hub 22 depicted in FIGS. 4-6.

Turning now to FIG. 5, the assembly of the stylet 20 in the introducer 10 is depicted showing the alignment of the lug 24 in the stylet hub 22 with the L-shaped slot 18 of the hub 16 of the introducer 10. In use, the stylet 20 is inserted into the lumen of the hub 16 and needle 12 so that the lug 24 enters the cut-out L-shaped opening 18. The hub 22 is thereafter rotated 90° in relation to the hub 16 thereby rotating the pin 24 until it seats in the position depicted in FIG. 6. The pin 24 is shown seated within the L-shaped opening 18, which may have a slight relief at the seating point depicted in FIG. 6.

With the stylet 20 fully inserted and locked in place within sheath lo, there is no possibility that the stylet will either rotate or back out during the penetration procedure.

Figure 7:
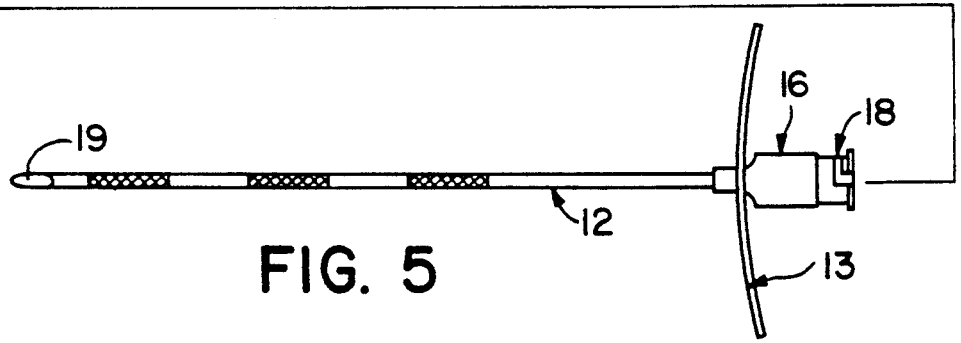
FIG. 7 is an enlarged detailed side view of the curved distal tip of the introducer needle in a further embodiment of the invention.

As depicted in FIG. 3, the distal tip 14 is straight. However, it will be understood that it may desirably be so constructed that when unrestrained, it assumes an angle of curvature of about 15°-18° in the direction of the opening 19, as shown in FIG. 7. The flexibility may be achieved by the use of certain flexible alloys, e.g., Elgiloy. In this embodiment, the normally curved tip 14 is straightened and strengthened by the introduction and locking of the stylet 20 as described in reference to FIG. 4-6. After withdrawal of stylet 20, the tip 14 may assume its curved shape within the epidural space to guide the lead 40 laterally into and advance it further into the epidural space as described in reference to FIGS. 1 and 2.

Although the preferred embodiments of the invention employ finger engageable wings 13 to facilitate the introduction of the stylet and needle introducer assembly, it will be understood that the invention may be practiced without such wings. Moreover, although a Huber point side opening 18 and tip configuration have been described, it will be understood that other opening and tip configurations, e.g., the more rounded Weiss and the short bevel Crawford needles, with matching tips 26 may also be used.

The above-described method, installation and access to the epidural space is, of course, greatly facilitated by using X-ray fluoroscopy, ultrasonic imaging and other known techniques during the installation and fixation. Accordingly, the various elements of the apparatus of the present invention are preferably formed of radio-opaque material.

It will be understood that the embodiments of the present invention which have been described are merely illustrative of some of the applications of the principles of the present invention. Numerous modifications may be made by those skilled in the art without departing from the true spirit and scope of the invention.

What is claimed is:

1. A method of introducing a flexible member into the epidural space of the spinal column of a patient employing an introducer assembly for achieving access to the epidural space comprising an epidural needle assembly, including an elongated needle having a side opening at its distal tip, a hub at its proximal tip and a lumen extending therebetween, and a stylet removable insertable within the lumen of said needle through said hub and having a beveled tip and a hub, comprising the steps of:

inserting said stylet into the lumen of said needle such that said lumen is filled by said stylet;

providing a locking mechanism on the hub of said stylet and a hub of said needle, wherein locking is effected by rotation of said stylet and said needle until the beveled tip of said stylet is aligned with the side opening of said needle;

rotating and locking said locking mechanism to align said beveled tip of said stylet with said side opening of said needle;

percutaneously inserting the locked needle and stylet assembly between the vertebrae in the patient's spine so that the tip of the epidural needle and stylet assembly is within said epidural space;

unlocking and withdrawing said stylet from the lumen of said needle;

inserting a flexible lead member through the lumen of said needle until the flexible member is positioned in said epidural space; and withdrawing said needle from the patient while leaving said flexible lead in said epidural space.

2. The method of claim 1 further comprising the additional step of filling the lumen of the needle with a saline solution upon removal of the stylet.

3. The method of claim 2 comprising the additional step of advancing said introducer needle into the epidural space following filling said lumen of said epidural needle with said saline solution.

4. The method of claim 1 wherein said step of inserting and locking said introducer assembly comprises the step of positioning said stylet in the cannula of a Tuohy needle.

5. The method of claim 1, wherein said step of inserting said lead comprises inserting a neurostimulator lead through the cannula of said introducer until said neurostimulator lead is positioned in the epidural space.

6. The method of claim I further comprising the steps of providing a lug projecting from said hub of said stylet and an L-shaped cut-out in said hub of said needle:

and wherein said rotating and locking step further comprises inserting and rotating said lug in said L-shaped cut-out whereby said stylet is locked in place by relative rotation of said stylet hub with respect to said needle hub to position said lug to a predetermined position in said L-shaped cut-out.

7. The method of claim 6 further comprising the step of providing said stylet and said needle with predetermined relative lengths such that said stylet, when in said locked position, completely fills the lumen of said needle and blocks said distal side opening thereof.

8. The method of claim 7 further comprising the steps of providing said stylet with a beveled distal tip set at a predetermined rotational angle to said lug whereby rotation of said lug to said predetermined position positions said beveled tip in line with said side opening.

9. In a method for introduction of a flexible lead member into the epidural space in the spinal column of a patient employing an epidural needle assembly comprising an elongated introducer needle having a flexible distal tip adapted to assume a predetermined curvature angle when unrestrained and a side opening at the distal tip opening in the direction of curvature, a lumen extending from the distal tip to a proximal hub attached to the needle at its proximal end and an elongated stylet having a hub at one end thereof and a pointed tip adapted to be positioned in the lumen of said needle to block the passage of fluids therethrough and to stiffen the needle, the improvement comprising the steps of:

locking the position of the stylet within said lumen of said needle and preventing relative axial or rotational motion therebetween;

percutaneously inserting said locked introducer needle and stylet assembly between the vertebrae in the patient's spine so that the tip of the assembly is positioned in the epidural space of the patient when the assembly is so inserted; and unlocking and withdrawing said stylet assembly to allow the needle distal tip to assume its predetermined curvature angle in the epidural space.

10. The method of claim 9 further comprising the steps of providing said lug projecting from said hub of said stylet and an L-shaped cut-out in said hub of said needle:

and wherein said locking step further comprises inserting and rotating said lug in said L-shaped cut-out whereby said stylet is locked in place by relative rotation of said stylet hub with respect to said needle hub to position said lug to a predetermined position in said L-shaped cut-out.

11. The method of claim 10 further comprising the step of providing said stylet and said needle with predetermined relative lengths such that said stylet, when in said locked position, completely fills the lumen of said needle and blocks said side opening thereof.

12. The method of claim 11 further comprising the step of providing said stylet with a beveled distal tip set at a predetermined rotational angle to said lug whereby rotation of said lug to said predetermined position positions said beveled tip adjacent said side opening and straightens the predetermined curvature of the tip.

13. Apparatus for introduction of a flexible lead member into the epidural space in the spinal column of a patient, comprising an epidural needle assembly comprising an elongated introducer needle having a side opening at its distal tip and a lumen extending from the distal tip to a proximal hub attached to the needle at its proximal end and an elongated stylet having a hub at one end thereof and a pointed tip adapted to be positioned in the lumen of said needle to block the passage of fluids therethrough and to stiffen the needle, wherein the improvement comprises:

a locking mechanism means comprising a first locking member on said hub of said needle and a second locking member on the hub of said stylet for locking the position of the stylet within said lumen of said needle and preventing relative axial or rotational motion therebetween, whereby said introducer needle and stylet assembly may be percutaneously inserted together between the vertebrae in the patient's spine so that the tip of the assembly are within the epidural space of the patient when the assembly is so inserted.

14. The apparatus of claim 13 wherein said stylet and said needle have predetermined relative lengths such that said stylet, when in said locked position, completely fills the lumen of said needle and blocks said side opening thereof.

15. The apparatus of claim 14 wherein said stylet has a beveled distal tip set at a predetermined rotational angle to said second locking member, whereby rotation of said stylet hub to said predetermined rotational angle positions said beveled tip in line with said side opening.

16. The apparatus of claim 13 wherein said elongated introducer needle distal tip is constructed to assume a predetermined angle of curvature adjacent to and in the direction of the side opening when said stylet is removed to provide a curved guide for the introduction of said flexible lead member into the epidural space.

17. The apparatus of claim 16 wherein said stylet and said needle have predetermined relative lengths such that said stylet, when in said locked position, completely fills the lumen of said needle and blocks said side opening thereof and straightens said predetermined angle of curvature.

18. The apparatus of claim 17 wherein said stylet has a beveled distal tip set at a predetermined rotational angle to said second locking member, whereby rotation of said stylet hub to said predetermined rotational angle positions said beveled tip in line with said side opening.

19. The apparatus of claim 18 wherein said locking means further comprises a lug projecting from said hub of said stylet and an L-shaped cut-out in said hub of said needle, and wherein said lug is adapted to be received in said L-shaped cut-out and said stylet is locked in place by relative rotation of said stylet hub with respect to said needle hub to advance and rotate said lug to a predetermined position in said L-shaped cut-out.

20. Apparatus for introduction of a flexible lead member into the epidural space in the spinal column of a patient, comprising an epidural needle assembly comprising an elongated introducer needle having a side opening at its distal tip and a lumen extending from the distal tip to a proximal hub attached to the needle at its proximal end and an elongated stylet having a hub at one end thereof and a pointed tip adapted to be positioned in the lumen of said needle to block the passage of fluids therethrough and to stiffen the needle, wherein the improvement comprises:

a locking mechanism comprising a first locking member on said hub of said needle and a second locking member on the hub of said stylet for locking the position of the stylet within said lumen of said needle and preventing relative axial or rotational motion there between, said first locking member comprising a lug projecting from said hub of said stylet and said second locking member comprising an L-shaped cut-out in said hub of said needle, and wherein said lug is adapted to be received in said L-shaped cut-out and said stylet is locked in place by relative rotation of said stylet hub with respect to said needle hub to advance and rotate said lug to a predetermine position in said L-shaped cut-out, whereby said introducer needle and stylet assembly may be percutaneously inserted together between the vertebrae in the patient's spine so that the tip of the assembly are within the epidural space of the patient when the assembly is so inserted.

21. The apparatus of claim 20 wherein said stylet and said needle have predetermined relative lengths such that said stylet, when in said locked position, completely fills the lumen of said needle and blocks said side opening thereof.

22. The apparatus of claim 21 wherein said stylet has a beveled distal tip set at a predetermined rotational angle to said lug whereby rotation of said lug to said predetermined position positions said beveled tip in line with said side opening.

* * * * *